United States Patent
Row et al.

(10) Patent No.: US 11,078,135 B2
(45) Date of Patent: Aug. 3, 2021

(54) SYSTEM FOR PRODUCING 1,3-BUTADIENE AND METHOD OF PRODUCING 1,3-BUTADIENE USING THE SYSTEM

(71) Applicant: Korea Kumho Petrochemical Co., Ltd., Seoul (KR)

(72) Inventors: Kyoung Ho Row, Daejeon (KR); Yong Hee Yun, Sejong-si (KR); Jin Woo Park, Dangjin-si (KR); Jae Woo Kim, Daejeon (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 0 days.

(21) Appl. No.: 16/707,384

(22) Filed: Dec. 9, 2019

(65) Prior Publication Data

US 2020/0181043 A1 Jun. 11, 2020

(30) Foreign Application Priority Data

Dec. 10, 2018 (KR) .................. 10-2018-0157800

(51) Int. Cl.
*B01J 8/02* (2006.01)
*C07C 5/48* (2006.01)
*C07C 5/32* (2006.01)
*C07C 11/167* (2006.01)

(52) U.S. Cl.
CPC .................... *C07C 5/48* (2013.01); *B01J 8/02* (2013.01); *B01J 8/0278* (2013.01); *C07C 5/322* (2013.01); *B01J 2208/00805* (2013.01); *B01J 2208/00893* (2013.01); *C07C 11/167* (2013.01)

(58) Field of Classification Search
CPC ... B01J 8/02; B01J 8/025; B01J 8/0278; B01J 2208/00805; B01J 2208/00893; C07C 5/3332; C07C 5/333; C07C 5/48; C07C 5/322
See application file for complete search history.

(56) References Cited

U.S. PATENT DOCUMENTS 3,925,498 A * 12/1975 Stadig ............... B01J 8/0453 585/625
2007/0244349 A1 10/2007 Crone et al.
2019/0016649 A1 * 1/2019 Kim ................. B01J 21/04

FOREIGN PATENT DOCUMENTS

| CN | 102516008 A | 6/2012 |
| CN | 102814150 B | 8/2014 |
| JP | 48-54104 A | 7/1973 |
| JP | 2016-203150 A | 12/2016 |
| KR | 10-2014-0128367 A | 11/2014 |
| KR | 10-2016-0083224 A | 7/2016 |
| KR | 10-1738403 B1 | 6/2017 |
| KR | 10-2018-0077702 A | 7/2018 |

* cited by examiner

*Primary Examiner* — Lessanework Seifu
(74) *Attorney, Agent, or Firm* — Novick, Kim & Lee, PLLC; Jae Youn Kim

(57) ABSTRACT

One aspect of the present disclosure provides a system for producing 1,3-butadiene, which includes: a first supply unit, by which a first feed including a butene raw material, oxygen and steam is supplied; a second supply unit, by which a second feed including a butene raw material and oxygen is supplied; and a reaction unit, which includes a catalyst fixed bed and in which an oxidative dehydrogenation reaction takes place, wherein the first supply unit is connected to a front end of the reaction unit, and the second supply unit is connected to an intermediate end of the reaction unit.

11 Claims, 5 Drawing Sheets

SYSTEM FOR PRODUCING 1,3-BUTADIENE AND METHOD OF PRODUCING 1,3-BUTADIENE USING THE SYSTEM

CROSS-REFERENCE TO RELATED APPLICATION

This application claims priority to and the benefit of Korean Patent Application No. 2018-0157800, filed on Dec. 10, 2018, the disclosure of which is incorporated herein by reference in its entirety.

BACKGROUND

1. Technical Field

The present disclosure relates to a system for producing 1,3-butadiene and a method of producing 1,3-butadiene using the system, and more particularly, to a system and a method for producing 1,3-butadiene from butene.

2. Description of Related Art 1,3-Butadiene is a compound used for producing synthetic rubber such as styrene-butadiene rubber (SBR), polybutadiene rubber (BR), a butadiene homopolymer or the like or acrylonitrile butadiene styrene (ABS) which is a thermoplastic resin.

Generally, 1,3-butadiene is produced by the pyrolysis of hydrocarbons using naphtha as a raw material (i.e. naphtha cracking). The naphtha cracking yields methane, ethane, ethene, acetylene, propane, propene, butene, butadiene, and a mixture of higher (C5 or more) hydrocarbons having 5 or more carbon atoms. However, the process efficiency of the pyrolysis method employed to produce 1,3-butadiene is low because other unsaturated hydrocarbons (olefins) are produced at the same time and thus excessive energy is consumed in separation and purification.

A method of directly dehydrogenating butane or butene using a heterogeneous catalyst may yield more 1,3-butadiene than the pyrolysis method does, but since the reaction is an endothermic reaction, there is a thermodynamic disadvantage, a high reaction temperature is required, and the catalyst is rapidly deactivated.

In a method of producing 1,3-butadiene through the oxidative dehydrogenation of butene, energy consumption can be minimized because the reaction is an exothermic reaction which proceeds at a relatively low temperature unlike the direct dehydrogenation reaction, and since an oxidizing agent may be added, the generation of carbon deposits (coke) can be suppressed.

Although advantages thereof have been described above, the oxidative dehydrogenation reaction requires the use of an oxidizing agent at high temperatures during the reaction, so a large amount of inert gas (nitrogen, carbon dioxide, steam, etc.) should be injected to stabilize the reaction. The use of an excessive amount of nitrogen in this case may increase the safety of the reaction, but may cause the problem such as a large amount of money being spent on the construction of facility due to the excessive amount of nitrogen gas and the generation of a product containing 1,3-butadiene in a post-reaction cooling process.

In this regard, a method of using steam instead of nitrogen for suppressing the generation of carbon deposits and removing reactor heat has been proposed. Since the steam can be removed as water in a cooling process, the size of the extraction distillation column may be made small, but there are problems such as waste water containing a large amount of organic matter is generated when cooling a hot product discharged from the reactor and an excessive amount of energy is used to cool the high-temperature steam to a low temperature.

According to Korean Patent Registration No. 10-1738403, when 1,3-butadiene is produced by way of supplying a part of the total oxygen input amount separately, a butene conversion rate and 1,3-butadiene yield may be improved, but due to the difficulty in dispersing generated heat which increases in proportion to the butene conversion rate and the 1,3-butadiene yield, problems such as the temperature of the catalyst bed increases and stability is lowered occur.

The above information disclosed in this section is merely for enhancement of understanding of the general background of the disclosure and therefore it may contain information that does not form the prior art that is already known in this country to a person of ordinary skill in the art.

SUMMARY OF THE DISCLOSURE

In order to address the above-described problems of the prior art, the present disclosure is directed to providing a system for producing 1,3-butadiene, which utilizes pure oxygen and provides ease of control of heat generation, and a method of producing 1,3-butadiene using the system.

Also, the present disclosure is directed to providing a system and a method for producing 1,3-butadiene, which allow a butene conversion rate and 1,3-butadiene yield to be improved and the generation of a side-product, carbon dioxide, to be controlled to a low level at the same time.

In addition, the present disclosure is directed to providing a method of producing 1,3-butadiene, in which steam that increases process costs is used less but the same or better effect is provided.

One aspect of the present disclosure provides a system for producing 1,3-butadiene, which includes: a first supply unit, by which a first feed including a butene raw material, oxygen and steam is supplied; a second supply unit, by which a second feed including a butene raw material and oxygen is supplied; and a reaction unit, which includes a catalyst fixed bed and in which an oxidative dehydrogenation reaction takes place, wherein the first supply unit is connected to a front end of the reaction unit, and the second supply unit is connected to an intermediate end of the reaction unit.

According to one embodiment, the number of the second supply unit may be one or more.

According to one embodiment, the second supply unit may be connected to a 25 to 75% point of the reaction unit.

According to one embodiment, the catalyst fixed bed may be a coating catalyst including an inert support, an intermediate and a catalyst component.

According to one embodiment, the catalyst fixed bed may include: a molded body (i), which includes a carrier coated with a catalyst mixture including a catalyst powder, an organic binder, an inorganic binder and water mixed at a weight ratio of 1.0:0.01 to 0.1:0.02 to 0.2:1.0 to 3.0; or a molded body (ii), which is formed by extrusion-molding a catalyst mixture including a catalyst powder, an organic binder, an inorganic binder and water mixed at a weight ratio of 1.0:0.01 to 0.1:0.02 to 0.2:0.02 to 0.2.

According to one embodiment, an amount of the butene raw material included in the first feed may be 40 to 90% by volume relative to a total amount of the butene raw material supplied to the system for producing 1,3-butadiene.

According to one embodiment, in the first feed and the second feed, the butene raw material and the oxygen may be included in a volume ratio of 1:0.5 to 1.2.

According to one embodiment, an amount of the steam may be 500 to 1,500% by volume relative to the total amount of the butene raw material supplied to the system for producing 1,3-butadiene.

Another aspect of the present disclosure provides a method of producing 1,3-butadiene, in which the above-described system for producing 1,3-butadiene is used.

According to one embodiment, the butene raw material may be converted at a rate of 70% or more.

According to one embodiment, the 1,3-butadiene may be produced with a yield of 60% or more.

According to one embodiment, the catalyst fixed bed may have a maximum temperature of 500° C. or less.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
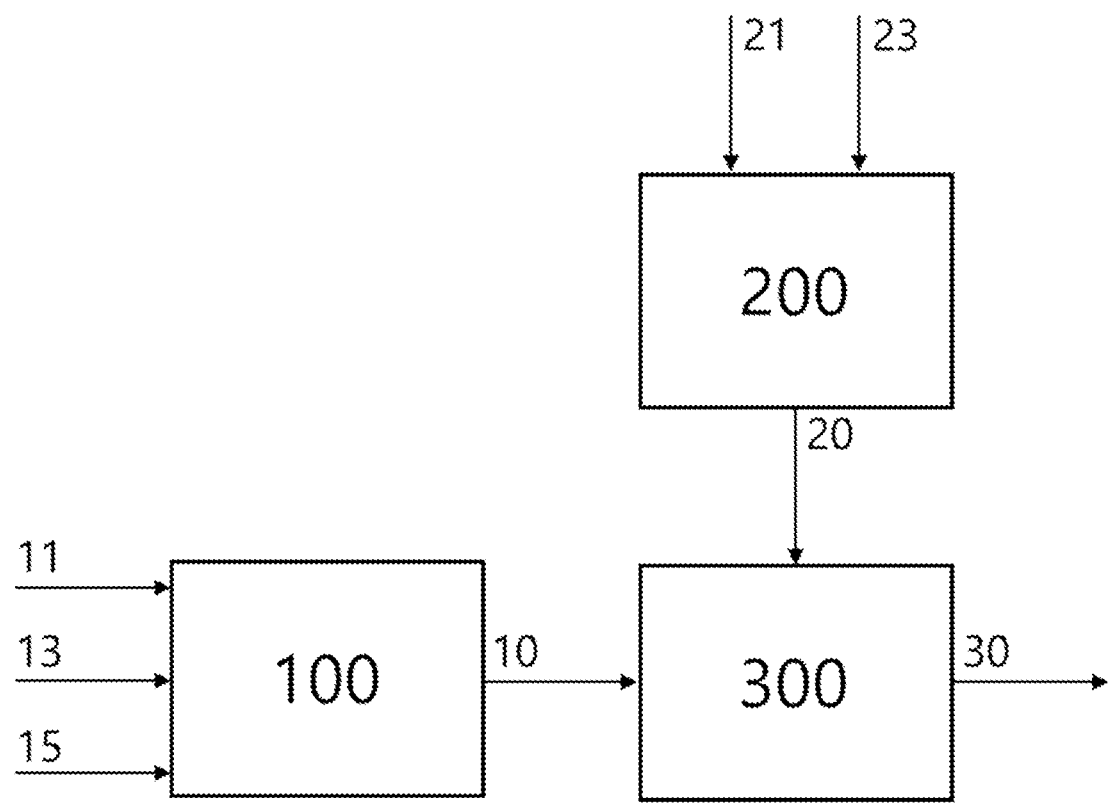
FIG. 1 is a schematic diagram of a system for producing 1,3-butadiene according to one embodiment of the present disclosure.

Hereinafter, the present disclosure will be described with reference to the accompanying drawings. However, it should be understood that the disclosure can be embodied in various forms and thus is not limited to the embodiments described herein. In addition, in order to clearly describe the disclosure, parts irrelevant to the description of the disclosure are omitted in the drawings, and like reference numerals designate like parts throughout the specification.

Throughout this specification, when a part is mentioned as being "connected" to another part, this means that the part may not only be "directly connected" to the other part but may also be "indirectly connected" to the other part through another member interposed therebetween. In addition, when a part is mentioned as "including" a specific component, this does not preclude the possibility of the presence of other component(s) in the part, which means that the part may further include the other component(s), unless otherwise stated.

When a numerical value is presented herein, the value has the precision of the significant digit provided in accordance with the standard rules in chemistry for significant digits unless its specific range is stated otherwise. For example, the numerical value 10 includes the range of 5.0 to 14.9, and the numerical value 10.0 includes the range of 9.50 to 10.49.

Hereinafter, embodiments of the present disclosure will be described in detail with reference to the accompanying drawings.

System for Producing 1,3-Butadiene

FIG. 1 is a schematic diagram of a system for producing 1,3-butadiene according to one embodiment of the present disclosure.

Referring to FIG. 1, the system for producing 1,3-butadiene according to one aspect of the present disclosure may include: a first supply unit 100, by which a first feed including a butene raw material, oxygen and steam is supplied; a second supply unit 200, by which a second feed including a butene raw material and oxygen is supplied; and a reaction unit 300, which includes a catalyst fixed bed and in which an oxidative dehydrogenation reaction takes place, wherein the first supply unit may be connected to a front end of the reaction unit, and the second supply unit may be connected to an intermediate end of the reaction unit.

The system for producing 1,3-butadiene may be realized in various ways or forms, but it is preferred that each facility is suitably arranged and designed for a continuous process considering aspects such as cost, efficiency and the like. In addition, depending on the capacity of the system for producing 1,3-butadiene, there may be provided one or more second supply units 200.

The first supply unit 100 may supply the first feed, which has been introduced through a butene raw material stream 11, an oxygen stream 13 and a steam stream 15, to a first feed stream 10 connected to a front end of the reaction unit 300, and the second supply unit 200 may supply the second feed, which has been introduced through a butene raw material stream 21 and an oxygen stream 23, to a second feed stream 20 connected to an intermediate end of the reaction unit 300. In this case, the first feed and the second feed may be independently passed through a mixer or directly supplied to the reaction unit 300 without a separate mixing process and used as a reactant. In this case, the butene raw material, the oxygen and the steam may be supplied with precision by a mass flow controller.

The first supply unit 100 or the second supply unit 200 may include a heater for increasing the temperature of the first or second feed to a reaction temperature, in which case, the temperature of the first or second feed may be increased to a temperature ranging from 150° C. or more, 200° C. or more, or 250° C. or more, and 500° C. or less, 450° C. or less, or 400° C. or less. When the temperature of the first or second feed is less than 150° C., the feed may cool the catalyst fixed bed inside the reaction unit 300, causing 1,3-butadiene yield to be reduced, and when temperature of the first or second feed exceeds 500° C., since heat generation at an upper portion of the reaction unit 300 is increased, side reactions may be promoted, causing 1,3-butadiene yield to be reduced. Once heated by the heater, the first or second feed may be transferred to the reaction unit 300 and used as a reactant for an oxidative dehydrogenation reaction.

The first feed and the second feed may be transferred to the reaction unit 300 through the first feed stream 10 and the second feed stream 20, respectively. In this case, the butene raw material, the oxygen and the steam inside the feeds may be either transferred in a mixed state or mixed inside the reaction unit 300 after being transferred separately. Preferably, the second supply unit 200 may supply the butene raw material and the oxygen separately. Specifically, the butene raw material and the oxygen may be supplied separately so that the raw material loss possibly caused due to side reactions can be prevented. The first feed and the second feed which are respectively supplied from the first supply unit 100 and the second supply unit 200 may be used as a reactant for an oxidative dehydrogenation reaction in the reaction unit 300 and converted into a product, 1,3-butadiene.

The 1,3-butadiene produced in the reaction unit 300 may be discharged from the reaction unit 300 through a product discharge flow 30 and then purified by a series of purification processes. Such purification processes may include cooling, compression, dehydration, absorption, degassing and distillation, but are not limited thereto, and any process known in the art may be freely selected and carried out.

In the present specification, the front end of the reaction unit 300 to which the first feed stream 10 is connected is defined as a 0% point, and the rear end of the reaction unit 300 to which the product discharge flow 30 is connected is defined as a 100% point. That is, an intermediate end of the reaction unit 300 refers to a position that is between the 0% point and the 100% point of the reaction unit 300, with both endpoints being excluded. In this case, the second supply unit 200 may be connected to a 25 to 75% point of the reaction unit 300, for example 25%, 35%, 45%, 55%, 65% or 75% point of the reaction unit 300, through the second feed stream 20. When the second supply unit 200 is connected to a less than 25% point of the reaction unit 300, an effect that is not different from what is provided by a system including only a first supply unit 100 and no second supply unit 200 may be provided, and when the second supply unit 200 is connected to a more than 75% point, the reactants supplied through the second feed stream 20 may not sufficiently react.

The reaction unit 300 may be provided with a reactor for producing 1,3-butadiene by subjecting the supplied reactants to an oxidative dehydrogenation reaction. The reactor may be a well-known reactor that is usable for an oxidative dehydrogenation reaction or a similar reaction, and is for example a multi-tubular reactor, a multistage reactor, or a reactor in which one or more thereof are connected in series, but the present disclosure is not limited thereto.

The reaction unit 300 may include a catalyst fixed bed, and the catalyst fixed bed may be provided as a single catalyst fixed bed or as a plurality of catalyst fixed beds which are spaced apart from one another. When the catalyst fixed bed is provided as a plurality of catalyst fixed beds which are spaced apart from one another, the second supply unit 200 may supply the second feed between the individual catalyst fixed beds. In this case, the volume or size of the individual catalyst fixed beds may be adjusted considering the relative volume ratio of the butene raw material and the oxygen supplied from the second supply unit 200.

When a powdery catalyst is simply loaded in the catalyst fixed bed, the uniformity of a catalyst powder dispersion during a reaction may be lowered, causing the surface area to become less consistent, and it is difficult to control reaction rates. Therefore, it is preferred that a molded body having a predetermined shape which is coated with a powdery catalyst or a molded body having a predetermined structure which is formed of a powdery catalyst is used as the catalyst fixed bed.

For example, the catalyst fixed bed may be a coated catalyst including an inert support, an intermediate and a catalyst component, and the catalyst fixed bed preferably includes: a molded body (i), which includes a carrier coated with a catalyst mixture including a catalyst powder, an organic binder, an inorganic binder and water mixed at a weight ratio of 1.0:0.01 to 0.1:0.01 to 0.2:0.1 to 3.0; or a molded body (ii), which is formed by extrusion-molding a catalyst mixture including a catalyst powder, an organic binder, an inorganic binder and water mixed at a weight ratio of 1.0:0.01 to 0.1:0.01 to 0.2:0.02 to 0.2.

The molded body (i) may be formed by uniformly coating a carrier having a certain range of cell density with a catalyst mixture including the above-described catalyst powder, an organic binder, an inorganic binder and water, performing drying at a temperature of 100 to 160° C., or 120 to 140° C., and then performing heat treatment at a temperature of 400 to 650° C., or 500 to 550° C. using an electric furnace. When the drying temperature is less than 100° C., the solution coating may flow down to result in an uneven dispersion of the catalyst mixture on the carrier surface. When the heat-treatment temperature is less than 400° C., it is difficult to remove the organic binder completely, and when the heat-treatment temperature is more than 650° C., the crystal structure of the catalyst mixture coating may be altered. The catalyst powder may be freely selected and used among the catalysts that are usable for an oxidative dehydrogenation reaction (e.g., ferrite powder). The carrier may have various shapes such as a honeycomb, a sphere, a cylinder, a clover, a star and the like.

The organic binder may be one selected from the group consisting of methyl cellulose, ethylene glycol, a polyol, a food oil, an organic fatty acid, and a mixture of two or more thereof, and is preferably hydroxyl methyl cellulose or polyvinyl alcohol, but the present disclosure is not limited thereto.

The inorganic binder may be one selected from the group consisting of solid-phase silica, solid-phase alumina, solid-phase silica-alumina, a silica sol, an alumina sol, water glass, and a mixture of two or more thereof, and is preferably fumed silica, a silica sol, boehmite or an alumina sol, but the present disclosure is not limited thereto.

The molded body (ii) may be formed by extruding the catalyst mixture into a predetermined shape using an extrusion-molding machine equipped with a mold, naturally drying the extrusion-molded body at 10 to 40° C., 15 to 35° C., or 20 to 25° C., and then performing heat treatment at a temperature of 400 to 650° C., or 500 to 550° C. using an electric furnace. When the heat-treatment temperature is less than 400° C., it is difficult to remove the organic binder completely, and when the heat-treatment temperature is more than 650° C., the crystal structure of the extrusion-molded catalyst mixture may be altered. The molded body may be freely extruded into any structure including a honeycomb shape, a cylindrical shape, a hole-type structure having an internal void(s), a structure having a clover leaflet-shaped or star-shaped protrusion(s) on the outside thereof, and the like. The structure of the molded body may be optimized while maintaining the contact area and strength thereof.

Meanwhile, the molded body may have a cell density of 50 to 800 cells per square inch (cpsi), or 100 to 600 cpsi. When the molded body has a cell density of less than 50 cpsi, since the surface area of the catalyst is small, the reaction activity thereof may be lowered, and when the molded body has a cell density of more than 800 cpsi, the cells may be clogged with the carbon deposits generated during an oxidative dehydrogenation reaction, causing the reaction pressure to be excessively increased.

The butene raw material may be added such that a total usage amount thereof is dividedly added through two or more streams 11 and 21. As the butene raw material, a butene mixture such as a C4 mixture or C4 raffinate may be used, and since 1,3-butadiene yield may be lowered due to catalyst activity deterioration or rapid heat generation when the iso-butene content of the butene raw material is above a certain level, it is preferred that either pure n-butene (1-butene or 2-butene) or a butene raw material in which an iso-butene content is maintained below a certain level is used.

The oxygen may be added such that a total usage amount thereof is dividedly added through two or more streams 13 and 23, and the oxygen may be pure oxygen. Although, conventionally, air containing oxygen and nitrogen was added or pure oxygen and pure nitrogen were simultaneously added for use as a diluent for the control of heat generation, there were economic disadvantages in that a reduction in the relative amount of oxygen actually required for a reaction led to a reduction in a production amount relative to a system size, and energy was wasted for steam production. However, in the present disclosure, since a butene raw material and oxygen are dividedly added through a first supply unit and one or more second supply units, the stability degradation issue of a catalyst fixed bed due to a high temperature can be addressed, and it is possible to produce 1,3-butadiene using pure oxygen and to provide a system for producing 1,3-butadiene having a smaller size than a conventional system for producing 1,3-butadiene.

The steam may serve to control the heat of reaction in an oxidative dehydrogenation reaction and to remove the carbon deposits generated on the surface of the catalyst fixed bed during a reaction, and may be supplied in a variety of ways or forms. For example, the steam may be supplied in the form of high-temperature and high-pressure steam or as the water supplied to an evaporator by a pump is vaporized into water vapor.

When the relative amount of oxygen is large in the oxidative dehydrogenation reaction, a butene raw material conversion rate and 1,3-butadiene yield may be increased, but the yield of a side-product, carbon dioxide, may be increased more rapidly, causing a raw material loss issue to be intensified. On the other hand, when the relative amount of oxygen is small, there is the disadvantage such as the conversion rate and the 1,3-butadiene yield are decreased, causing process costs to be increased due to the reuse of raw materials.

When the relative amount of steam is large, although 1,3-butadiene yield may be increased, and generated heat may be easily dissipated such that catalyst stability may be improved, since an excessive amount of energy is used for the formation of such steam, process costs can be reduced only when the 1,3-butadiene yield relative to the usage amount of steam is increased.

The amount of the butene raw material contained in the first feed may be 40 to 90% by volume or 55 to 75% by volume relative to the total amount of the butene raw material supplied to the system for producing 1,3-butadiene, and the remaining 10 to 60% or 25 to 45% by volume of the total amount of the butene raw material may be supplied through the second feed. When the first feed accounts for less than 40% by volume of the butene raw material, the conversion rate of the butene raw material may be reduced and thus overall process efficiency may be lowered, and when the first feed accounts for more than 90% by volume of the butene raw material, it may be difficult to realize the effect of divided addition provided by the use of the second feed.

In the first feed and the second feed, the butene raw material and the oxygen may be included in a volume ratio of 1:0.5 to 1.2 or 1:0.7 to 1. When the volume of the oxygen is less than 0.5 relative to a butene raw material volume of 1, it is difficult to facilitate an oxidative dehydrogenation reaction, and when the volume of the oxygen is more than 1.2 relative to a butene raw material volume of 1, as the amount of oxygen relative to that of butene becomes excessively large such that a complete oxidation reaction becomes dominant, the relative amount of a side-product, carbon dioxide, in the product may be increased.

The amount of the steam may be 500% or more, 600% or more, or 700% or more by volume, and 1,500% or less, 1,400% or less, 1,300% or less, or 1,200% or less by volume relative to the total amount of the butene raw material supplied to the system for producing 1,3-butadiene. When the amount of the steam is less than 500% by volume, 1,3-butadiene yield may be reduced, and catalyst stability may be reduced due to heat generation, and when the amount of the steam is more than 1,500% by volume, there may be an economic disadvantage.

Since the system for producing 1,3-butadiene dividedly supplies the butene raw material and the oxygen, the amount of the steam is large relative to that of the butene raw material at every point of the reaction unit 300, and therefore, an excellent butene conversion rate, excellent 1,3-butadiene yield, excellent control of heat generation, and reduced side-product (carbon dioxide) generation can be realized at the same time.

Method of Producing 1,3-Butadiene

In the method of producing 1,3-butadiene according to another aspect of the present disclosure, the above-described system for producing 1,3-butadiene may be used.

The system for producing 1,3-butadiene, and the types, amounts and effects of various raw materials are the same as described above.

According to the method of producing 1,3-butadiene, the butene raw material may be converted at a rate of 70% or more, or 70 to 80%, the 1,3-butadiene may be obtained with a yield of 60% or more, or 60 to 70%, and the catalyst fixed bed may have a maximum temperature of 500° C. or less.

An efficient oxidative dehydrogenation reaction is carried out at 250 to 500° C. At a temperature of less than 250° C., since the catalyst is not activated, it is difficult to facilitate a partial oxidation reaction, and at a temperature of more than 500° C., as catalyst stability may be reduced, a phase change may occur, carbon deposits may be generated on the catalyst fixed bed surface at an increased rate, and as a complete oxidation reaction becomes dominant over a partial oxidation reaction, the relative amount of a side-product, carbon dioxide, in the product may be increased.

Generally, the butene raw material conversion rate and the 1,3-butadiene yield can be improved by carrying out a reaction at a higher temperature. However, according to the production method of the present disclosure, it is possible to attain a butene raw material conversion rate of 70% or more and a 1,3-butadiene yield of 60% or more while maintaining the temperature of the catalyst fixed bed at 500° C. or less.

Therefore, when the production method of the present disclosure is used, the catalyst lifetime is longer than in a conventional production method and thus process efficiency is considerably higher, and it is possible to prevent the occurrence of safety accidents.

Hereinafter, exemplary embodiments of the present disclosure will be described in more detail. However, hereinafter, only experimental results obtained from a few selected exemplary embodiments of the disclosure will be described, and the scope and contents of the disclosure should not be interpreted as being reduced or limited by the few selected exemplary embodiments. The effects of each of the various embodiments of the disclosure which are not explicitly set forth below will be described in detail in relevant sections.

Preparation Example: Preparation of Catalyst Molded Body

An alumina sol was prepared by mixing 1.76 g of boehmite, 4.5 g of water and 0.225 g of nitric acid. Three hundred milliliters of silica-alumina balls were added thereto, and the balls were rotated to uniformly attach the alumina sol to the balls. After drying at room temperature, additional drying was carried out at 80° C. for eight hours, and then heat treatment was carried out at 800° C. for four hours to prepare a ball-type silica-alumina carrier coated with gamma-alumina (weight of alumina sol coating/volume of alpha-alumina ball=5 g/L).

After uniformly mixing 95.3 g of a magnesium-ferrite metal oxide catalyst powder, 2.1 g of methyl cellulose and 16.2 g of water, 300 mL of the ball-type silica-alumina carrier coated with gamma-alumina was added thereto, and rotation was carried out such that the carrier was coated with the catalyst powder. After drying at room temperature, additional drying was carried out at 80° C. for eight hours, and then heat treatment was carried out at 550° C. for four hours to prepare a ball-type catalyst molded body coated with a ferritic metal oxide (weight of catalyst powder coating/volume of alpha-alumina ball coated with alumina sol=300 g/L).

Comparative Examples 1 to 9

The molded body of Preparation Example was loaded into a stainless steel reactor with a space velocity of 400 h$^{-1}$, and was activated at 370° C. A mixed gas including a C4 mixture (n-butene), oxygen and steam mixed in a volume ratio as shown in Table 1 was supplied to the stainless steel reactor through an upper portion of the reactor, and an oxidative dehydrogenation reaction was induced to prepare 1,3-butadiene.

Examples 1 to 6

The molded body of Preparation Example was loaded into a stainless steel reactor with a space velocity of 400 h$^{-1}$, and was activated at 370° C. After a first mixed gas including a butene raw material (C4), oxygen (O2) and steam mixed in a volume ratio as shown in Table 1 was supplied to the stainless steel reactor through an upper portion of the reactor and a second mixed gas including a butene raw material and oxygen mixed in a volume ratio as shown in Table 1 was supplied to a 50% point relative to the top of the molded body, an oxidative dehydrogenation reaction was induced to prepare 1,3-butadiene.

The reaction conditions of each of Examples and Comparative Examples were calculated using Equation 1 to Equation 4, and are summarized in Table 1.

Figure 2:
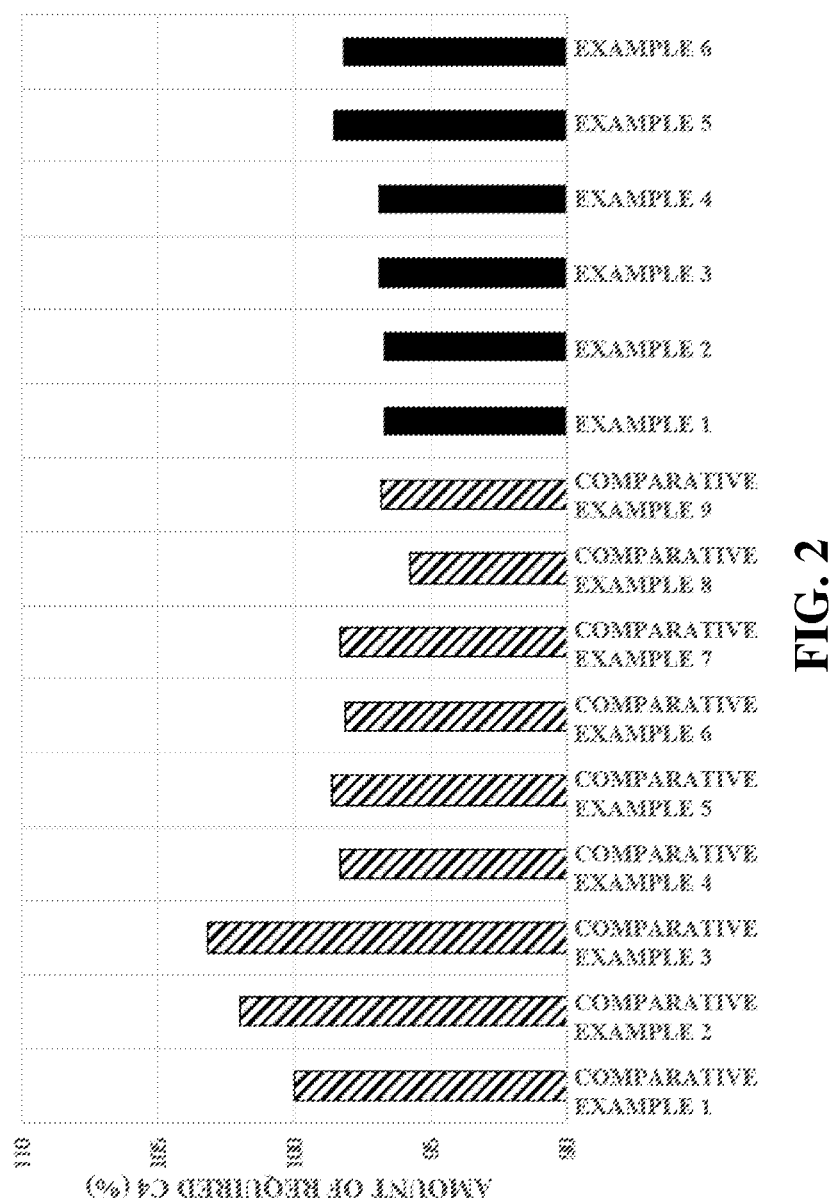
FIG. 2 shows the amount of a butene raw material required for producing the same amount of 1,3-butadiene in each of Examples of the present disclosure and Comparative Examples based on Comparative Example 1.

In addition, the amount of a butene raw material required for producing the same amount of 1,3-butadiene in each of Examples and Comparative Examples based on Comparative Example 1 is illustrated in FIG. 2.

The "Raw material input ratio" describes the volume ratio of a butene raw material, pure oxygen and steam, and in the case of Examples, the volume ratio of a butene raw material and pure oxygen is separately described for a first mixed gas and a second mixed gas, in the form of "first mixed gas+second mixed gas."

$$\text{Ratio of steam of } C4 = \frac{\text{Volume of supplied steam}}{\text{Volume of supplied } C4 \text{ mixture}} \quad \text{[Equation 1]}$$

$$C4 \text{ conversion rate (\%)} = \frac{\text{Weight of reacted } C4 \text{ mixture}}{\text{Weight of supplied } C4 \text{ mixture}} \times 100 \quad \text{[Equation 2]}$$

$$BD \text{ yield (\%)} = \frac{\text{Weight of produced 1,3-butadiene}}{\text{Weight of reacted } C4 \text{ mixture}} \times 100 \quad \text{[Equation 3]}$$

$$CO_2 \text{ yield (\%)} = \frac{\text{Weight of produced } CO_2}{\text{Weight of reacted } C4 \text{ mixture}} \times 100 \quad \text{[Equation 4]}$$

TABLE 1

| Classification | Raw material input ratio (C4:O$_2$:steam) | Ratio of steam to C4 (Steam/C4) | C4 conversion rate (%) | BD yield (%) | CO$_2$ yield (%) | Maximum temperature of catalyst bed (° C.) |
|---|---|---|---|---|---|---|
| Comparative Example 1 | 100:65:750 | 7.5 | 63.1 | 52.6 | 5.4 | 509 |
| Comparative Example 2 | 100:75:750 | 7.5 | 67.8 | 55.4 | 6.1 | 521 |
| Comparative Example 3 | 100:85:750 | 7.5 | 68.2 | 55.1 | 6.9 | 539 |
| Comparative Example 4 | 90:59:750 | 8.3 | 63.3 | 53.7 | 5.2 | 499 |
| Comparative Example 5 | 80:52:750 | 9.4 | 64.6 | 54.6 | 5.3 | 487 |
| Comparative Example 6 | 70:46:750 | 10.7 | 65.2 | 55.4 | 5.2 | 477 |
| Comparative Example 7 | 60:39:750 | 12.5 | 67.2 | 57.0 | 5.2 | 462 |
| Comparative Example 8 | 50:33:750 | 15 | 65.2 | 56.8 | 5.0 | 454 |
| Comparative Example 9 | 40:26:750 | 18.8 | 63.4 | 54.6 | 5.0 | 443 |
| Example 1 | 90 + 10:59 + 28:750 | 8.3 + 17.4 | 79.8 | 68.8 | 6.6 | 502 |
| Example 2 | 80 + 20:52 + 31:750 | 9.4 + 15.5 | 77.8 | 67.1 | 6.4 | 485 |
| Example 3 | 70 + 30:46 + 36:750 | 10.7 + 13.8 | 75.3 | 64.8 | 6.2 | 479 |

TABLE 1-continued

| Classification | Raw material input ratio (C4:O$_2$:steam) | Ratio of steam to C4 (Steam/C4) | C4 conversion rate (%) | BD yield (%) | CO$_2$ yield (%) | Maximum temperature of catalyst bed (° C.) |
|---|---|---|---|---|---|---|
| Example 4 | 60 + 40:39 + 39:750 | 12.5 + 12.6 | 73.8 | 63.5 | 6.0 | 467 |
| Example 5 | 50 + 50:33 + 43:750 | 15.0 + 11.4 | 72.3 | 61.1 | 6.0 | 463 |
| Example 6 | 40 + 60:26 + 47:750 | 18.8 + 10.3 | 71.0 | 60.3 | 5.8 | 465 |

Referring to Table 1 and FIG. 2, compared to Comparative Examples in which raw materials were supplied only through an upper portion of a reactor, a higher C4 conversion rate and a higher butadiene (BD) yield were exhibited in Examples in which part of a butene raw material and oxygen was supplied through a middle portion of a reactor, and the fact that the amount of a butene raw material required in Examples was only about 96% of what was required in Comparative Example 1 implies that Examples provide greater economic advantages.

When specifically examining the result based on Comparative Example 1, in Comparative Examples 2 and 3 in which the relative amount of supplied oxygen was increased, the conversion rate was increased, but also CO$_2$ generation was increased, such that the amount of a butene raw material required for producing the same amount of butadiene was increased.

In Comparative Examples 4 to 9, since the amount of butene and oxygen relative to that of steam was small, a maximum temperature of the catalyst bed was reduced, and stability was accordingly improved. However, although the amount of a butene raw material required for producing the same amount of butadiene was decreased due to reduced CO$_2$ generation, since the conversion rate was relatively low, it was required that an increased amount of raw materials were reused, which led to economic disadvantages such as an increase in the size of the reaction system and an increase in additional process costs for the material reuse.

On the other hand, in Examples 1 to 6 in which the relative amount of a butene raw material and oxygen was maintained small as in Comparative Examples 4 to 9 and at the same time an additional amount of the butene raw material and oxygen were supplied to a middle portion of a reactor, the butene conversion rate and the butadiene yield were significantly increased, and at the same time, a maximum temperature of the catalyst bed was lowered compared to Comparative Example 1. As a result, the stability was improved, and since the amount of a butene raw material required for producing the same amount of butadiene as well as the amount of raw materials to be reused was reduced, excellent economic advantages were provided.

Figure 3:
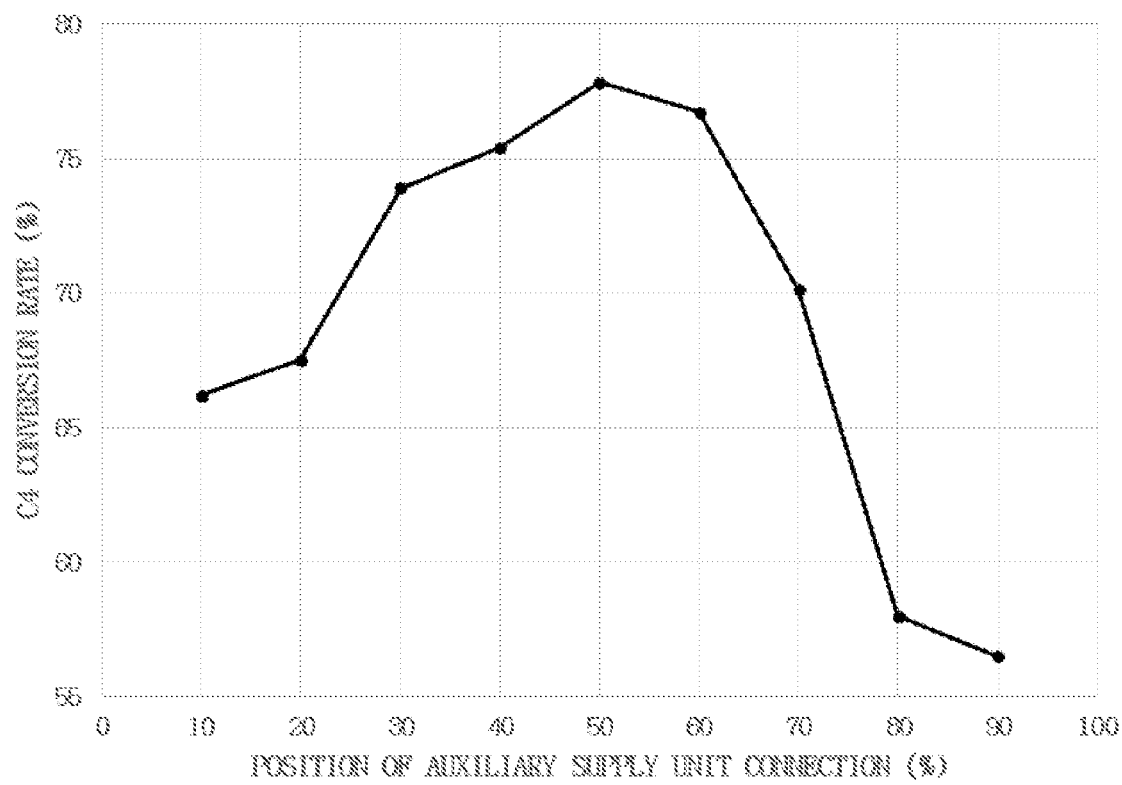
FIG. 3 illustrates the butene raw material conversion rates measured while varying the position of a second supply unit connection according to one embodiment of the present disclosure.
Figure 4:
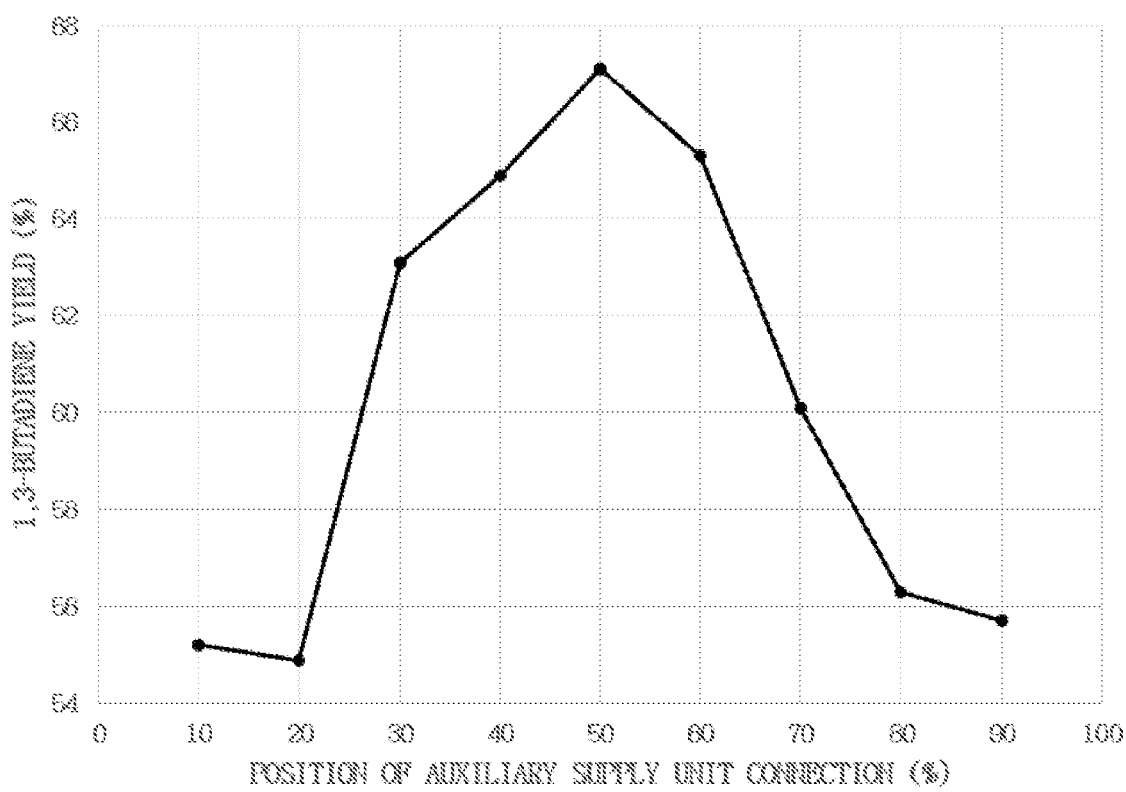
FIG. 4 illustrates the 1,3-butadiene yield measured while varying the position of a second supply unit connection according to one embodiment of the present disclosure.
Figure 5:
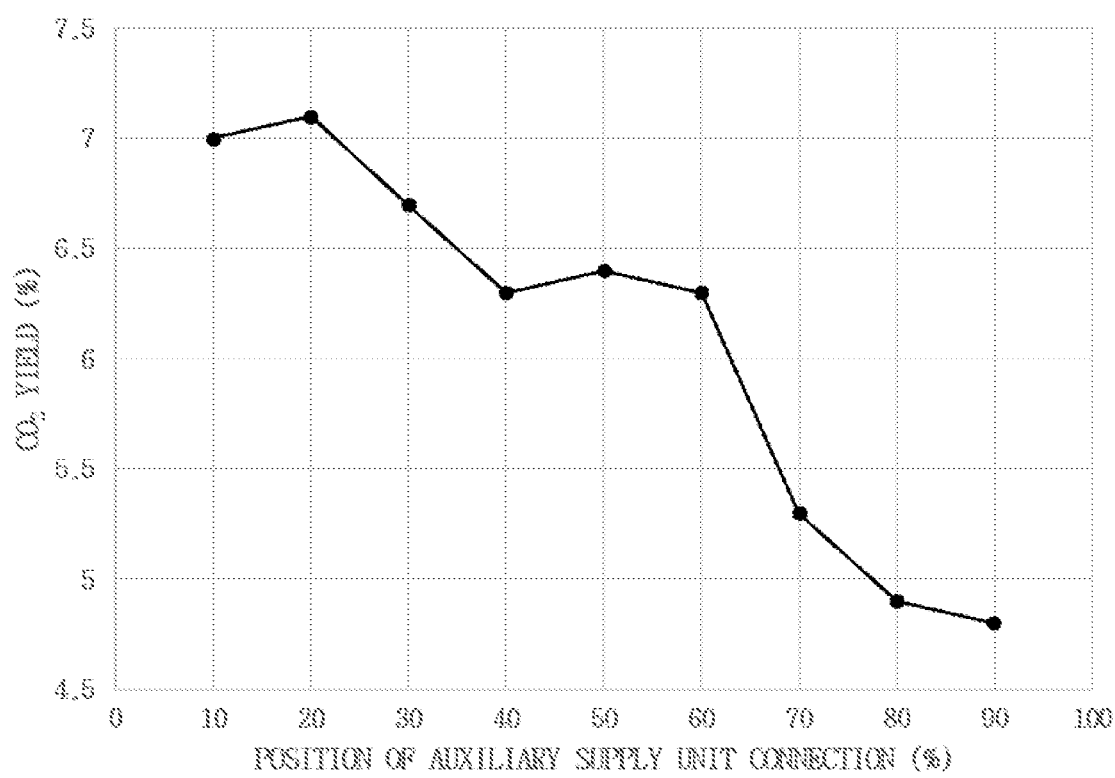
FIG. 5 illustrates the carbon dioxide yield measured while varying the position of a second supply unit connection according to one embodiment of the present disclosure.

An additional experiment was carried out by producing 1,3-butadiene in the same manner as in Examples except that a second supply unit for supplying a C4 mixture and oxygen was connected to a 20%, 30%, 40%, 60% 70% or 80% point relative to the top of the molded body, and results thereof, a C4 conversion rate, 1,3-butadiene yield and CO$_2$ yield, are illustrated in FIGS. 3 to 5.

Referring to FIGS. 3 to 5, it can be seen that when the C4 mixture and oxygen were supplied to the 10%, 20%, 80% or 90% point, a C4 conversion rate and a butadiene yield which were not significantly different from those of Comparative Examples were attained, whereas when the C4 mixture and oxygen were supplied to the 30% to 70% point, the above-described excellent advantageous effects of Examples were provided.

It is speculated that such a result was obtained because when a second supply unit is connected to a less than 20% point or a more than 80% point relative to the top of a reactor, either an effect which was not significantly different from what was provided by supplying all the materials through an upper portion of the reactor was provided or the additionally supplied raw materials could not sufficiently react.

According to one aspect of the present disclosure, it is possible to improve catalyst stability by easily controlling heat generation even while using pure oxygen.

According to another aspect of the present disclosure, it is possible to improve a butene conversion rate and 1,3-butadiene yield and control the generation of a side-product, carbon dioxide, to a low level at the same time.

According to still another aspect of the present disclosure, it is possible to produce the same or better effect in the production of 1,3-butadiene even while using less of the steam that increases process costs.

However, it is to be understood that the effects of the present disclosure are not limited to the above-described effects and include all effects deducible from the configuration of the disclosure described in the detailed description of the disclosure or in the claims.

The foregoing description of the present disclosure is intended for illustration, and it will be understood by those skilled in the art to which the disclosure pertains that the disclosure can be easily modified and implemented in various other forms without changing the technical spirit or essential features of the disclosure. Therefore, it should be understood that the embodiments described above are only exemplary in all aspects and not limiting. For example, each of the constituents described as being one combined entity may be implemented separately, and similarly, constituents described as being separate entities may be implemented in a combined form.

It should be understood that the scope of the present disclosure is defined by the following claims and that all changes or modifications derived from the meaning and scope of the claims and their equivalents are included in the scope of the disclosure.

DESCRIPTION OF SYMBOLS

10: FIRST FEED STREAM
11: BUTENE RAW MATERIAL STREAM
13: OXYGEN STREAM
15: STEAM STREAM
20: SECOND FEED STREAM
21: BUTENE RAW MATERIAL STREAM
23: OXYGEN STREAM
30: PRODUCT DISCHARGE FLOW

100: FIRST SUPPLY UNIT
200: SECOND SUPPLY UNIT
300: REACTION UNIT

What is claimed is:

1. A system for producing 1,3-butadiene, the system comprising:
   a first supply unit configured to supply a first feed including a butene raw material, oxygen and steam;
   a second supply unit configured to supply a second feed including a butene raw material and oxygen; and
   a reaction unit, which includes a catalyst fixed bed and in which an oxidative dehydrogenation reaction is to be taken place,
   wherein the first supply unit is connected to a front end of the reaction unit, and the second supply unit is connected to an intermediate end of the reaction unit, and
   wherein the first feed supplied by the first supply unit includes the butene raw material in an amount of 40% to 90% by volume relative to a total amount of the butene raw material supplied to the system.

2. The system of claim 1, wherein of the second supply unit has a plurality of supply units.

3. The system of claim 1, wherein the second supply unit is connected to a point located at 25% to 75% in a length from the front end of the reaction unit.

4. The system of claim 1, wherein the catalyst fixed bed is a coated catalyst including an inert support, an intermediate, and a catalyst component.

5. The system of claim 4, wherein the catalyst fixed bed includes:
   a molded body (i), which includes a carrier coated with a catalyst mixture including a catalyst powder, an organic binder, an inorganic binder and water mixed at a weight ratio of 1.0:0.01 to 0.1:0.02 to 0.2:1.0 to 3.0; or
   a molded body (ii), which is formed by extrusion-molding a catalyst mixture including a catalyst powder, an organic binder, an inorganic binder and water mixed at a weight ratio of 1.0:0.01 to 0.1:0.02 to 0.2:0.02 to 0.2.

6. The system of claim 1, wherein the first supply unit is configured to supply the first feed including the butene raw material, an amount of which is 40% to 90% by volume relative to a total amount of the butene raw material supplied to the system.

7. The system of claim 1, wherein the first and second supply units are configured to respectively supply the first feed and the second feed, respectively including the butene raw material and the oxygen in a volume ratio of 1:0.5 to 1.2.

8. The system of claim 1, wherein the first supply unit is configured to supply the first feed including the steam, an amount of which is 500% to 1,500% by volume relative to a total amount of the butene raw material supplied to the system.

9. A method for producing 1,3-butadiene in a system, the method comprising:
   supplying, by a first supply unit, a first feed including a butene raw material, oxygen and steam:
   supplying, by a second supply unit, a second feed including a butene raw material and oxygen; and
   allowing an oxidative dehydrogenation reaction to take place in a reaction unit including a catalyst fixed bed,
   wherein the first supply unit is connected to a front end of the reaction unit, and the second supply unit is connected to an intermediate end of the reaction unit, and
   wherein the first feed supplied by the first supply unit includes the butene raw material in an amount of 40% to 90% by volume relative to a total amount of the butene raw material supplied to the system.

10. The method of claim 9, wherein the butene raw material is converted at a rate of 70% or more.

11. The method of claim 9, wherein the 1,3-butadiene is produced with a yield of 60% or more.

* * * * *